US00PP11047P

United States Patent [19]

Zary

[11] Patent Number: Plant 11,047

[45] Date of Patent: Aug. 31, 1999

[54] HYBRID TEA ROSE PLANT NAMED 'JACRETTE'

[75] Inventor: Keith W. Zary, Thousand Oaks, Calif.

[73] Assignee: Bear Creek Gardens, Inc., Medford, Oreg.

[21] Appl. No.: 09/028,292

[22] Filed: Feb. 24, 1998

[51] Int. Cl.[6] ..... A01H 5/00

[52] U.S. Cl. ..... Plt./140

[58] Field of Search ..... Plt./139, 140

*Primary Examiner*—Howard J. Locker

*Attorney, Agent, or Firm*—Klarquist Sparkman Campbell Leigh & Whinston, LLP

[57] ABSTRACT

Hybrid tea rose plant having bright red flower color; long, straight stems; long vase life; tolerance to long distance shipping; upright, vigorous growth; and good cut flower production.

1 Drawing Sheet

The present invention relates to a new and distinct variety of rose plant of the hybrid tea class which was originated by me by crossing the variety 'JACcol', U.S. Plant Pat. No. 8,289, with the variety 'JACkar' (not patented.)

The primary objective of this breeding was to produce a new rose variety having bright red flower color, long stems, good vase life and shipping tolerance, good production of cut flowers, and a vigorous, upright growing habit. The objective was substantially achieved, along with other desirable improvements, as evidenced by the following unique combination of characteristics that are outstanding in the new variety and that distinguish it from its parents, as well as from all other varieties of which I am aware:

1. Bright red flower color;
2. Long, straight stems;
3. Long vase life;
4. Tolerant to long distance shipping;
5. Upright, vigorous growth; and
6. Good cut flower production.

'JACrette' produces 160–170 flowers per square meter of greenhouse with stems averaging 24–28 inches long. 'JACrette' has also shown good tolerance to shipping, it rehydrates well and lasts in the vase 10–12 days.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACcol', U.S. Plant Pat. No. 8,289.

*Pollen parent.*—'JACkar', not patented.

Classification:

*Botanical.*—Rosa hybrida.

*Commercial.*—Hybrid tea.

FLOWER

Observations made from specimens grown in a greenhouse environment at Somis, Calif., from January 1997 to February 1998.

Blooming habit: Continuous.

Bud:

*Size.*—About 1¾ inches long when the petals start to unfurl.

*Form.*—Long, pointed ovoid.

*Color.*—When sepals first divide, bud color is Red Group 53A. When half blown, the upper sides of the petals are Red Group 46A, and the lower sides of the petals are Red Group 53A.

*Sepals.*—Color: Green Group 138B. Surface texture: Covered in fine hairs. There are three normally to heavily appendaged sepals. There are two unappendaged sepals with hairy edges.

*Receptacle.*—Color: Yellow-Green Group 146D. Shape: Funnel. Size: Large (about ½"×5/16"). Surface: Smooth.

*Peduncle.*—Length: Long (averaging about 4"). Surface: Prickly. Color: Green Group 146D. Strength: Stiff, erect, heavy.

Bloom:

*Size.*—Large. Average open size is about 4–4½".

*Borne.*—Singly.

*Stems.*—Long (average about 24–28"), strong.

*Form.*—When first open: High centered. Permanence: Retains its form to the end, outer petals curl slightly.

*Petalage.*—Number of petals under normal conditions: 30–35.

*Color.*—The upper sides of the petals are Red Group 46A. The reverse sides of the petals are Red Group 53A. The base of each petal has a small (3/16"×3/16"), distinctive, Yellow Group 7C half moon at the point of attachment. The major color on the upper sides is Red Group 46A.

*Variegations.*—Occasional whitish streak on the guard petals.

*Discoloration.*—At the end of the first day: No change. At the end of the third day: No change. By day 9 or 10, there is a change to Red Group 53B, then on day 11 to Red Group 53C (in the vase), followed on day 12 by petal drop. On the plant, there is no color change through day six, then color changes to Red Group 53C followed on day 8 by petal drop.

*Fragrance.*—Moderate.

Petals:

*Texture.*—Thick.

*Shape.*—Round to slightly deltoid.

*Form.*—Tips slightly recurved.

*Arrangement.*—Imbricated. Petaloids in the center: Few, small.

*Persistence.*—Petals drop off cleanly before drying.

*Lastingness.*—On the plant: Long (8 days). As a cut flower: Long (10–12 days).

Reproductive parts:

*Anthers.*—Size: Large. Quantity: Many. Color: Yellow. Arrangement: Regular around styles.

*Filaments.*—Color: Reddish.

*Pollen.*—Color: Gold yellow.

*Styles.*—Color: Reddish.

*Stigmas.*—Color: Greenish white.

Plant:

*Form.*—Bush.

*Growth.*—Vigorous; upright; branching. At maturity, in the greenhouse after one year, height is six feet, width is four feet.

Foliage:

*Number of leaflets on normal mid-stem leaves.*—Five.

*Size.*—Large (7"×6½").

*Quantity.*—Abundant.

*Color.*—New foliage: Upper and lower sides: Greyed-Red Group 178A. Old foliage: Upper side: Green Group 139A. Lower side: Green Group 138C.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish (Greyed-Purple Group 187A.)

*Petiole underside.*—Smooth.

*Stipules.*—Medium (⅝"), serrated.

*Disease resistance.*—Susceptible to mildew under normal growing conditions at Somis, Calif.

Wood:

*New wood.*—Color: Reddish (Greyed-Purple Group 183C.) Bark: Smooth.

*Old wood.*—Color: Green (Green Group 137C with some purplish cast close to Greyed-Purple 183C.) Bark: Smooth.

Prickles:

*Quantity.*—On main canes from base: Ordinary. On laterals from main canes: Ordinary.

*Form.*—Medium (5/16"), hooked downward.

*Color when young.*—Red (Greyed-Purple Group 183C.)

Small prickles:

*Quantity.*—On main stalks: None. On laterals: None.

I claim:

1. A new and distinct variety of rose plant of the hybrid tea class, as herein shown and described, characterized particularly by bright red flower color; long, straight stems; long vase life; tolerance to long distance shipping; upright, vigorous growth; and good cut flower production.

* * * * *

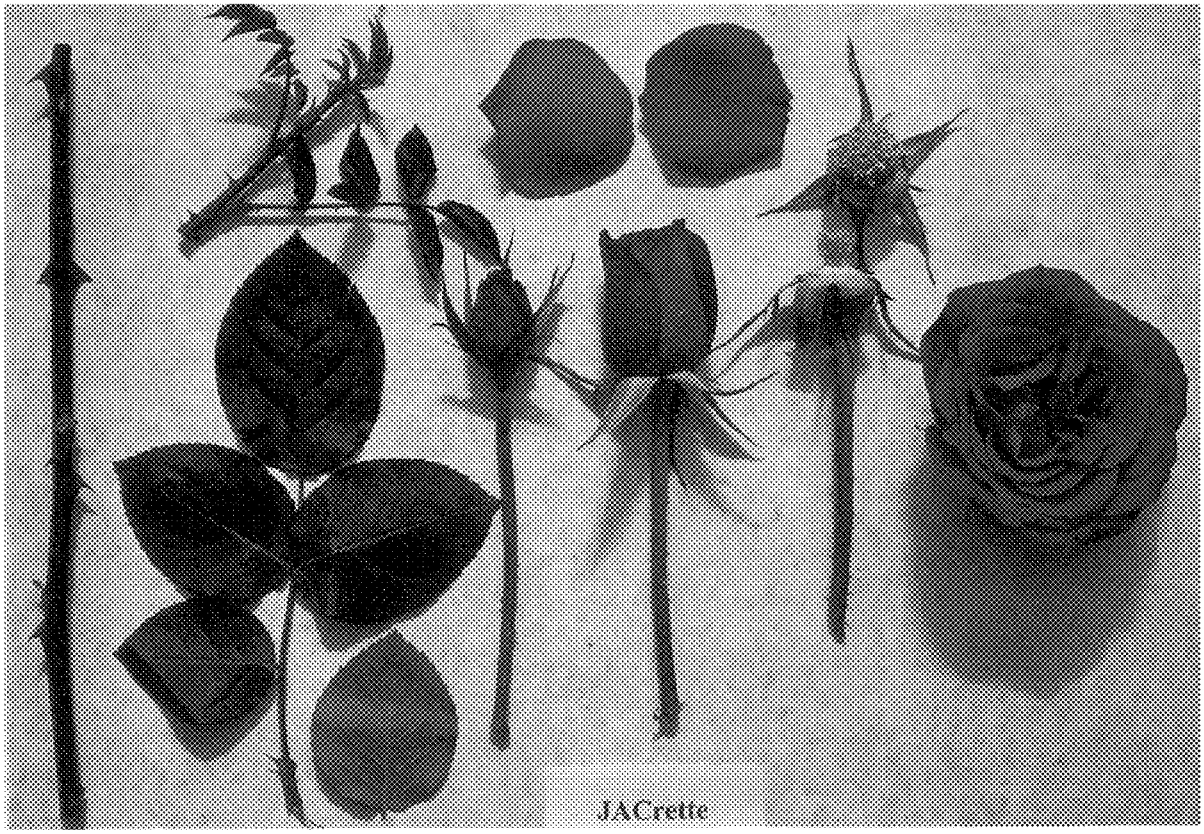
JACrette